United States Patent [19]

Hiramatsu et al.

[11] 4,367,350

[45] Jan. 4, 1983

[54] PROCESS FOR PREPARING PERFLUORO(LOWER)ALKYL-BENZENES AND THEIR DERIVATIVES

[75] Inventors: Uji Hiramatsu, Takatsuki; Toshihide Honda, Toyonaka; Yohnosuke Ohsaka, Takasuki, all of Japan

[73] Assignee: Daikin Kogyo Co., Ltd., Osaka, Japan

[21] Appl. No.: 864,804

[22] Filed: Dec. 27, 1977

[30] Foreign Application Priority Data

Dec. 27, 1976 [JP] Japan ................................. 51-159034

[51] Int. Cl.³ .............................................. C07C 17/14
[52] U.S. Cl. .................................... 570/144; 570/145
[58] Field of Search .................... 260/651 F; 570/144, 570/145

[56] References Cited

U.S. PATENT DOCUMENTS

| | | | |
|---|---|---|---|
| 2,062,743 | 12/1936 | Daudt et al. | 260/651 F |
| 2,121,330 | 1/1938 | Scherer et al. | 260/651 F |
| 3,755,477 | 8/1973 | Firth et al. | 260/651 F |
| 4,012,453 | 3/1977 | Nychka et al. | 260/651 F |
| 4,080,392 | 3/1978 | Ryf | 260/651 F |

*Primary Examiner*—Charles F. Warren
*Assistant Examiner*—Joseph A. Boska
*Attorney, Agent, or Firm*—Birch, Stewart, Kolasch & Birch

[57] ABSTRACT

A process for preparing perfluoro(lower)alkylbenzenes and derivatives thereof which comprises contacting a lower alkylbenzene or the corresponding derivative with hydrogen fluoride in the presence of chlorine in a gaseous phase at an elevated temperature to give the corresponding perfluoro(lower)alkylbenzene or its derivative.

9 Claims, No Drawings

PROCESS FOR PREPARING PERFLUORO(LOWER)ALKYL-BENZENES AND THEIR DERIVATIVES

The present invention relates to a process for preparing perfluoro(lower)alkylbenzenes and derivatives thereof. More particularly, it relates to a process for the preparation of perfluoro(lower)alkylbenzenes and derivatives thereof by reacting lower alkylbenzenes or the derivatives corresponding thereto with hydrogen fluoride in a gaseous phase.

For production of benzotrifluoride or its derivatives, there has been usually adopted a process which comprises reacting benzotrichloride or the corresponding derivative with hydrogen fluoride as a fluorinating agent [cf. U.S. Pat. No. 1,964,244, U.S. Pat. No. 3,136,822; Japanese Patent Publication (unexamined) No. 77324/1975]. In industrial practice, this reaction is normally effected in a liquid phase in an autoclave under an elevated pressure. However, the expense of the starting material (i.e. benzotrichloride or its derivative) in such a process takes a large proportion of the cost of the final product. Further, care must be taken concerning the stability in operation and the safety in working, since the reaction is performed under an elevated pressure. In addition, an expensive high pressure reaction apparatus is needed.

For overcoming the above drawbacks, attempts have been made to react toluene or its derivatives, which is much cheaper than benzotrichloride or its derivatives, with hydrogen fluoride so as to produce benzotrifluoride or a derivative thereof in one step. As the result, it has been found that such reaction does not proceed materially, but the presence of chlorine in the reaction system enables the selective substitution of the hydrogen atoms on the carbon atom in the methyl group as the side chain with the fluorine atom in the hydrogen fluoride to give benzotrifluoride or a derivative thereof. Advantageously, this selective substitution is applicable not only to toluene and its derivatives but also to other lower alkylbenzenes and their derivatives. The present invention is based on the above finding.

According to the present invention, there is provided a process for preparing a perfluoro(lower)alkylbenzene or a derivative thereof which comprises contacting a lower alkylbenzene or a derivative corresponding thereto with hydrogen fluoride in the presence of chlorine in a gaseous phase at an elevated temperature.

In the process of this invention, the starting material is a lower alkylbenzene or a derivative thereof (hereinafter referred to as "alkylbenzene compound"). The lower alkyl group in the lower alkylbenzene may usually have 1 to 4 carbon atoms, examples thereof being methyl, ethyl, propyl, isopropyl, butyl, etc. As the derivative of the lower alkylbenzene, there may be used any compound having a chemical structure constituted with a benzene ring and at least one lower alkyl group thereon. In addition to at least one lower alkyl group, one or more of substituents which do not materially interfere with the reaction between the lower alkyl group and hydrogen fluoride may be optionally present on the benzene ring. Examples of such substituents are nitro, cyano, halogen (e.g. chlorine, bromine, iodine), etc. Thus, the term "alkylbenzene compound" includes those compounds of the formula:

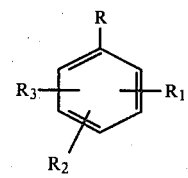

wherein R is lower alkyl, and $R_1$, $R_2$ and $R_3$ are each hydrogen, trichloromethyl, nitro, cyano or halogen. The lower alkyl group on the benzene ring may be partially halogenated. In other words, the alkylbenzene compounds wherein the hydrogen atoms in the lower alkyl group are partly substituted, for instance, with chlorine or bromine atoms are also usable as the starting material.

The molar ratio of hydrogen fluoride to be used with respect to the alkylbenzene compound is usually from about 3 to 15, preferably from about 3.3 to 12. The molar ratio of chlorine with respect to the alkylbenzene compound is normally from about 2 to 15, preferably from about 2.5 to 9. When the amount of chlorine is less than the said lower limit, the reaction does not substantially proceed. The use of chlorine in a higher amount than the said upper limit does not produce any advantage and may be rather unfavorable in producing a loss of the space or capacity.

Since the reaction in the process of this invention is generally exothermic, the control of the temperature during the reaction is usually desirable in order to avoid the drastic progress of the reaction, the thermal decomposition of the starting and produced materials, the by-production of tars, etc. For this purpose, the use of a gaseous diluent in the reaction system is recommended. A preferred gaseous diluent is one affording no unfavorable influence onto the proceeding of the reaction and having a large thermal capacity. Examples of such gaseous diluents are nitrogen, argon, hydrogen chloride, perhaloalkanes having 1 to 3 carbon atoms (the halogen atom being fluorine or chlorine), sulfur hexafluoride, etc. The amount of the gaseous diluent to be used is dependent upon its thermal capacity and may be usually from about 5 to 20 moles to one mole of the alkylbenzene compound.

In carrying out the process of the present invention, designed amounts of the alkylbenzene compound, of hydrogen fluoride and of chlorine may be charged together with the gaseous diluent, for instance, in a pre-heating apparatus and heated to make a gaseous mixture. The gaseous mixture is introduced into a reactor in a tubular shape, whereby the reaction proceeds at an elevated temperature. The reaction mixture exhausted from the reactor is introduced into a distillation tower, and gaseous materials such as hydrogen chloride, hydrogen fluoride and chlorine are taken out from the top of the tower while liquid materials including the produced perfluoro(lower)alkylbenzene or its derivative are obtained from the bottom of the tower.

The reactor may be made of any material resistant to corrosion by hydrogen fluoride, hydrogen chloride, chlorine and the like at an elevated temperature. Examples of such materials are stainless steel, nickel, nickel alloy (e.g. Iconel, Hastelloy), etc.

The elevated temperature in the reactor is varied with the kind of the alkylbenzene compound and may be usually from about 350° to 600° C., preferably from about 400° to 550° C. Particularly when the temperature is about 450° C. or higher, the chlorination on the benzene ring may proceed simultaneously with the fluorination of the lower alkyl group as the side chain. The contact time in the reactor is not limitative but is usually from about 5 to 40 seconds. A higher temperature or a longer contact time over the said upper limits will unfavorably result in the increased production of tars or by-products. The pressure in the reactor is usually atmospheric but may be reduced or elevated.

The thus obtained liquid materials comprise perfluoro(lower)alkylbenzene or a derivative thereof (hereinafter referred to as "perfluoroalkylbenzene compound"), which corresponds to the starting alkylbenzene compound. The derivative of the perfluoro(lower)alkylbenzene may be the compound having a chemical structure constituted with a benzene ring and at least one perfluoro(lower)alkyl group thereon. In addition to at least one perfluoro(lower)alkyl group, one or more substituents such as nitro, cyano, halogen and the like may be present on the benzene ring. Thus, the term "perfluoroalkylbenzene compound" includes those of the formula:

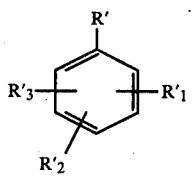

wherein R' is perfluoro(lower)alkyl, and R'$_1$, R'$_2$ and R'$_3$ are each hydrogen, trifluoromethyl, nitro, cyano or halogen. As stated above, the chlorination may sometimes proceed on the benzene ring depending on the reaction conditions, particularly the temperature. In such case, there is more or less produced the perfluoroalkylbenzene compound substituted with a chlorine atom(s) on the benzene ring.

Recovery of the perfluoroalkylbenzene compound from the liquid materials may be carried out by a per se conventional separation procedure such as distillation.

The process of this invention is industrially advantageous in producing perfluoroalkylbenzenes or their derivatives, which are useful as intermediates in the synthesis of various medicaments, agricultural chemicals, dyestuffs, etc., efficiently in high yields. Since the reaction can proceed even under atmospheric pressure without using any specific catalyst, the expense for the reaction apparatus and the reagent is greatly saved. It is particularly advantageous in comparison with the conventional process requiring two steps (i.e. chlorination of toluene and fluorination of benzotrichloride) that the conversion of alkylbenzene compounds into perfluoroalkylbenzene compounds is accomplished in a single step.

Practical and presently preferred embodiments of the invention are illustratively shown in the following Examples where % and part(s) are by weight unless otherwise indicated.

EXAMPLES 1–6

Designed amounts of toluene, chlorine and hydrogen fluoride together with a gaseous diluent were charged in a pre-heating apparatus, and the contents were heated up to a certain temperature. The resulting gaseous mixture was introduced into a "Hastelloy C" made tubular reactor (inner volume, 150 ml) with regulation of the feed amount, and the reaction was effected under the conditions as shown in Table 1. The reaction product coming out of the reactor was transferred to a distillation tower and distilled there.

From the top of the distillation tower, low boiling impurities such as hydrogen chloride, hydrogen fluoride and chlorine were exhausted, and from the bottom of the tower, the residual liquid substances were obtained. This liquid was subjected to gas chromatographic analysis (stationary phase: Silicone SE 30; column, 3 m; temperature-elevating rate, 5° C./min). The results are shown in Table 1.

TABLE 1

| | | Reaction conditions | | | | | | Reaction products (mol %) | | | |
| --- | --- | --- | --- | --- | --- | --- | --- | --- | --- | --- | --- |
| Example | Diluent | Diluent/Toluene (molar ratio) | Pre-heating temp. (°C.) | Reaction temp. (°C.) | Chlorine/Toluene (molar ratio) | HF/Toluene (molar ratio) | Contact time (sec.) | BTF and its monochlorinated derivatives*[1] | BHDF*[2] | BCDF*[3] | Unreacted toluene | Others*[4] |
| 1 | Carbon tetrachloride | 9.8 | 390 | 475 | 6.0 | 9.4 | 19.0 | 71 | 3 | 13 | 0 | 13 |
| 2 | Carbon tetrachloride | 9.8 | 390 | 465 | 9.4 | 7.0 | 20.3 | 69 | 4 | 11 | 0 | 16 |
| 3 | Carbon tetrachloride | 9.9 | 445 | 470 | 2.5 | 5.3 | 39.4 | 69 | 0 | 2 | 0 | 29 |
| 4 | Sulfur hexafluoride | 9.6 | 390 | 465 | 9.1 | 6.8 | 19.7 | 63 | 9 | 8 | 0 | 20 |
| 5 | Carbon tetrachloride | 9.1 | — | 475 | 5.8 | 8.0 | 19.8 | 61 | 30 | 7 | 0 | 2 |
| 6 | Carbon tetra- | 10.0 | 360 | 370 | 8.8 | 5.2 | 25.9 | 21 | 30 | 11 | 1 | 37 |

TABLE 1-continued

| | | Reaction conditions | | | | | | Reaction products (mol %) | | | | |
| --- | --- | --- | --- | --- | --- | --- | --- | --- | --- | --- | --- | --- |
| Example | Diluent | Diluent/Toluene (molar ratio) | Pre-heating temp. (°C.) | Reaction temp. (°C.) | Chlorine/Toluene (molar ratio) | HF/Toluene (molar ratio) | Contact time (sec.) | BTF and its monochlorinated derivatives*1 | BHDF*2 | BCDF*3 | Unreacted toluene | Others*4 |
| | chloride | | | | | | | | | | | |

Note:
[1] Trifluoromethylbenzene and its monochlorinated derivative on the benzene ring.
[2] Difluoromethylbenzene.
[3] Difluorochloromethylbenzene.

[4]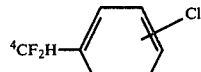

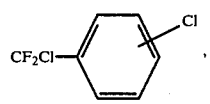

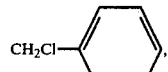

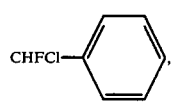

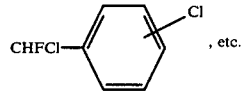, etc.

EXAMPLE 7

In the same manner as in Example 1, a gaseous mixture of benzyl chloride, hydrogen fluoride and chlorine diluted with carbon tetrachloride was subjected to reaction. The results are shown in Table 2.

TABLE 2

| Reaction conditions | |
| --- | --- |
| Diluent (molar ratio to benzyl chloride) | CCl₄ (9.8) |
| Pre-heating temperature (°C.) | 370 |
| Heating temperature (°C.) | 460 |
| Chlorine (molar ratio to benzyl chloride) | 8.4 |
| Hydrogen fluoride (molar ratio to benzyl chloride) | 6.0 |
| Contact time (sec.) | 20.1 |
| Reaction products (mol %) | |
| Trifluoromethylbenzene | 55 |
| Monochlorinated derivative of trifluoromethylbenzene on the benzene ring | 9 |
| Difluoromethylbenzene | 12 |
| Unreacted benzyl chloride | 0 |
| Others | 24 |

EXAMPLE 8 and 9

In the same manner as in Example 1, a gaseous mixture of p-chlorotoluene, hydrogen fluoride and chlorine diluted with carbon tetrachloride was subjected to reaction. The results are shown in Table 3.

TABLE 3

| Example | 8 | 9 |
| --- | --- | --- |
| Reaction conditions | | |
| Diluent (molar ratio to p-chlorotoluene) | CCl₄ (10.0) | CCl₄ (10.0) |
| Pre-heating temperature (°C.) | 410 | 390 |
| Heating temperature (°C.) | 470 | 465 |
| Chlorine (molar ratio to p-chlorotoluene) | 8.7 | 9.4 |
| Hydrogen fluoride (molar ratio to p-chlorotoluene) | 6.7 | 7.0 |
| Contact time (sec.) | 21.2 | 19 |
| Reaction products (mol %) | | |
| Monochlorinated derivative of trifluoromethylbenzene on the benzene ring | 78 | 71 |
| Dichlorinated derivative of trifluoromethylbenzene on the benzene ring | 5 | 4 |
| Monochlorinated derivative of difluoromethylbenzene on the benzene ring | 13 | 19 |
| Unreacted p-chlorotoluene | 0 | 0 |
| Others | 4 | 6 |

What is claimed is:

1. A process for preparing perfluoro(lower)alkylbenzenes which comprises contacting a lower alkylbenzene with hydrogen fluoride in the absence of any catalyst in the gaseous phase and in the presence of chlorine at an elevated temperature to give the corresponding perfluoro(lower)alkylbenzene.

2. The process according to claim 1, wherein the hydrogen fluoride is used in a molar ratio of about 3 to 15 with respect to the lower alkylbenzene.

3. The process according to claim 1, wherein the chlorine is used in a molar ratio of about 2 to 15 with respect to the lower alkylbenzene.

4. The process according to claim 1, wherein the contact is effected at a temperature of about 350° to 600° C.

5. The process according to claim 4, wherein the temperature is from about 450° to 600° C.

6. The process according to claim 1, wherein the contact is effected for a period of about 5 to 40 seconds.

7. The process according to claim 1, wherein the contact is effected in the presence of a gaseous diluent.

8. The process according to claim 1, wherein the lower alkylbenzene is toluene.

9. The process according to claim 1, wherein the hydrogen fluoride is used in a molar ratio of about 3 to 15 and the chlorine is used in a molar ratio of about 2 to 15 with respect to the lower alkylbenzene.

* * * * *